United States Patent [19]
Swanson et al.

[11] Patent Number: 6,113,612
[45] Date of Patent: Sep. 5, 2000

[54] MEDICAL ANASTOMOSIS APPARATUS

[75] Inventors: William J. Swanson; Mark D. Wahlberg, both of St. Paul; Jason A. Galdonik, Minneapolis; Todd Allen Berg, Plymouth; Scott P. Thome, St. Cloud, all of Minn.

[73] Assignee: St. Jude Medical Cardiovascular Group, Inc., Minneapolis, Minn.

[21] Appl. No.: 09/186,774

[22] Filed: Nov. 6, 1998

[51] Int. Cl.⁷ .............................. A61B 17/08; A61F 2/06
[52] U.S. Cl. ................................. 606/153; 623/1
[58] Field of Search ...................... 606/153, 151, 606/152, 154, 194, 192, 198; 623/1, 12

[56] References Cited

U.S. PATENT DOCUMENTS

| | | | |
|---|---|---|---|
| 4,214,587 | 7/1980 | Sakura, Jr. | |
| 4,503,569 | 3/1985 | Dotter . | |
| 4,592,754 | 6/1986 | Gupte et al. | 623/1 |
| 4,617,932 | 10/1986 | Kornberg . | |
| 4,665,906 | 5/1987 | Jervis . | |
| 4,787,899 | 11/1988 | Lazarus | 623/1 |
| 5,104,399 | 4/1992 | Lazarus | 623/1 |
| 5,135,467 | 8/1992 | Citron | 600/16 |
| 5,207,695 | 5/1993 | Trout | 606/153 |
| 5,211,658 | 5/1993 | Clouse | 623/1 |
| 5,211,683 | 5/1993 | Maginot . | |
| 5,234,447 | 8/1993 | Kaster et al. | 606/153 |
| 5,275,622 | 1/1994 | Lazarus et al. | 623/1 |
| 5,304,220 | 4/1994 | Maginot | 623/1 |
| 5,316,023 | 5/1994 | Palmaz et al. | 128/898 |
| 5,354,336 | 10/1994 | Kelman et al. | 623/6 |
| 5,387,235 | 2/1995 | Chuter | 623/1 |
| 5,397,345 | 3/1995 | Lazarus | 623/1 |
| 5,397,355 | 3/1995 | Marin et al. | 623/12 |
| 5,443,497 | 8/1995 | Venbrux | 623/1 |
| 5,452,733 | 9/1995 | Sterman et al. | 128/898 |
| 5,456,712 | 10/1995 | Maginot | 623/1 |
| 5,489,295 | 2/1996 | Piplani et al. | 623/1 |
| 5,507,769 | 4/1996 | Marin et al. | 606/198 |
| 5,522,880 | 6/1996 | Barone et al. | 623/1 |
| 5,545,214 | 8/1996 | Stevens | 623/2 |
| 5,562,728 | 10/1996 | Lazarus et al. | 623/1 |
| 5,676,670 | 10/1997 | Kim | 606/108 |
| 5,695,504 | 12/1997 | Gifford, III et al. | 606/153 |
| 5,755,778 | 5/1998 | Kleshinski | 623/1 |
| 5,843,164 | 12/1998 | Frantzen et al. | 623/1 |
| 5,843,170 | 12/1998 | Ahn | 623/1 |
| 5,843,175 | 12/1998 | Frantzen | 623/1 |

FOREIGN PATENT DOCUMENTS

| | | |
|---|---|---|
| 670239 | 1/1994 | Australia . |
| 539237 A1 | 4/1993 | European Pat. Off. . |
| 0 637 454 A1 | 2/1995 | European Pat. Off. . |
| 0 680 734 A2 | 11/1995 | European Pat. Off. . |
| 0 684 022 A2 | 11/1995 | European Pat. Off. . |
| 0 701 800 A1 | 3/1996 | European Pat. Off. . |
| 0 712 614 A1 | 5/1996 | European Pat. Off. . |
| 489316 | 7/1938 | United Kingdom . |
| 2269104 | 2/1994 | United Kingdom . |
| WO 89/08433 | 9/1989 | WIPO . |

(List continued on next page.)

*Primary Examiner*—Michael Buiz
*Assistant Examiner*—Vikki Trinh
*Attorney, Agent, or Firm*—Fish & Neave; Robert R. Jackson

[57] ABSTRACT

A connector for use in providing an anastomotic connection between two tubular body fluid conduits in a patient. The connector is preferably a single, integral, plastically deformable structure that can be cut from a tube. The connector has axial spaced portions that include members that are radially outwardly deflectable from other portions of the connector. The connector is annularly enlargeable so that it can be initially delivered and installed in the patient in a relatively small annular size and then annularly enlarged to provide the completed anastomosis. The radially outwardly deflected members of the first and second portions respectively engage the two body fluid conduits connected at the anastomosis and hold those two conduits together in fluid-tight engagement. Apparatus for use in delivering and deploying a connector is also disclosed.

67 Claims, 11 Drawing Sheets

FOREIGN PATENT DOCUMENTS

| | | |
|---|---|---|
| WO 93/00868 | 1/1993 | WIPO . |
| WO 93/20757 | 10/1993 | WIPO . |
| WO 94/01056 | 1/1994 | WIPO . |
| WO 95/21592 | 8/1995 | WIPO . |
| WO 96/14808 | 5/1996 | WIPO . |
| WO 96/18361 | 6/1996 | WIPO . |
| WO 96/22745 | 8/1996 | WIPO . |
| WO 96/25897 | 8/1996 | WIPO . |
| WO 97/13463 | 4/1997 | WIPO . |
| WO 97/13471 | 4/1997 | WIPO . |

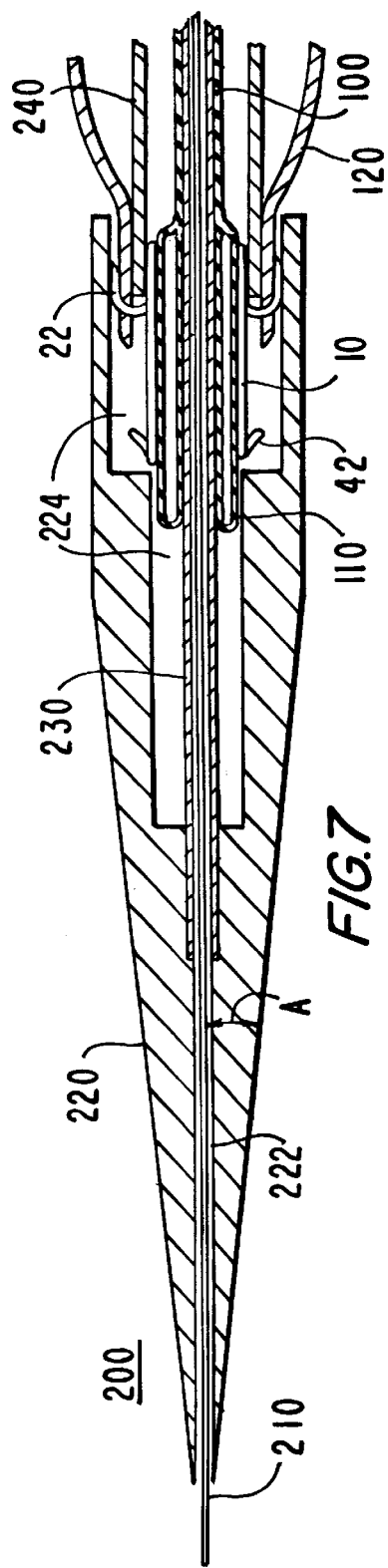
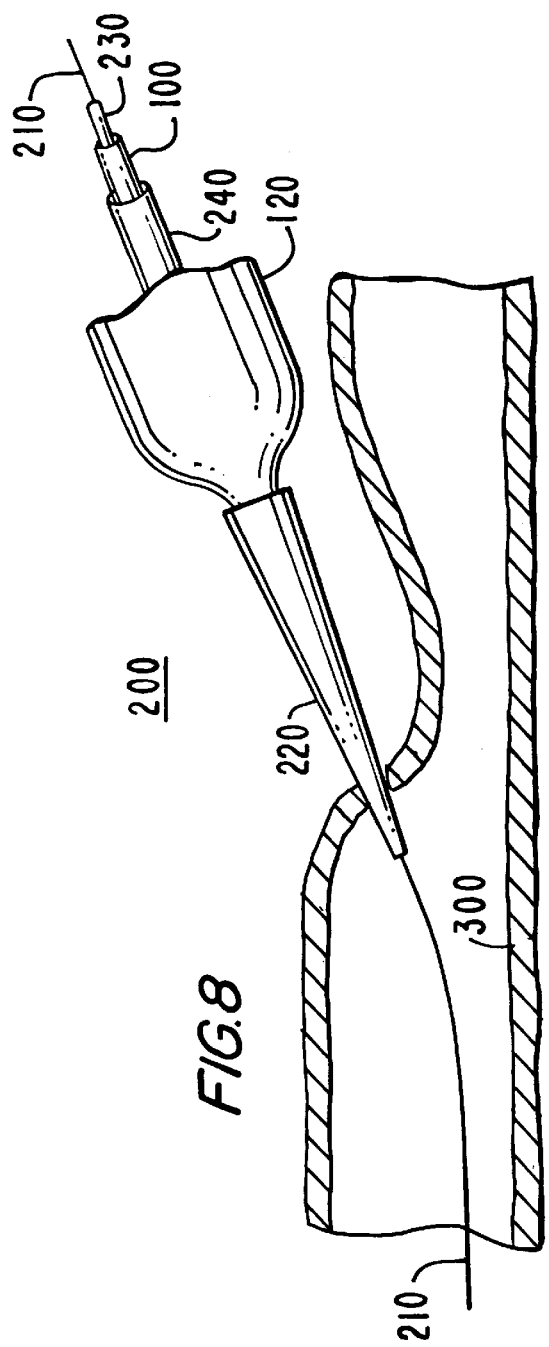

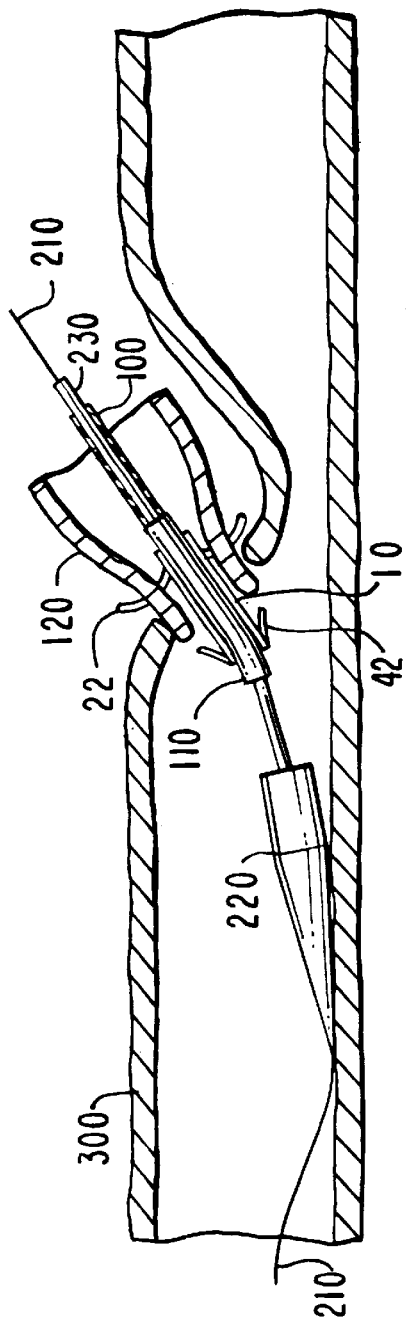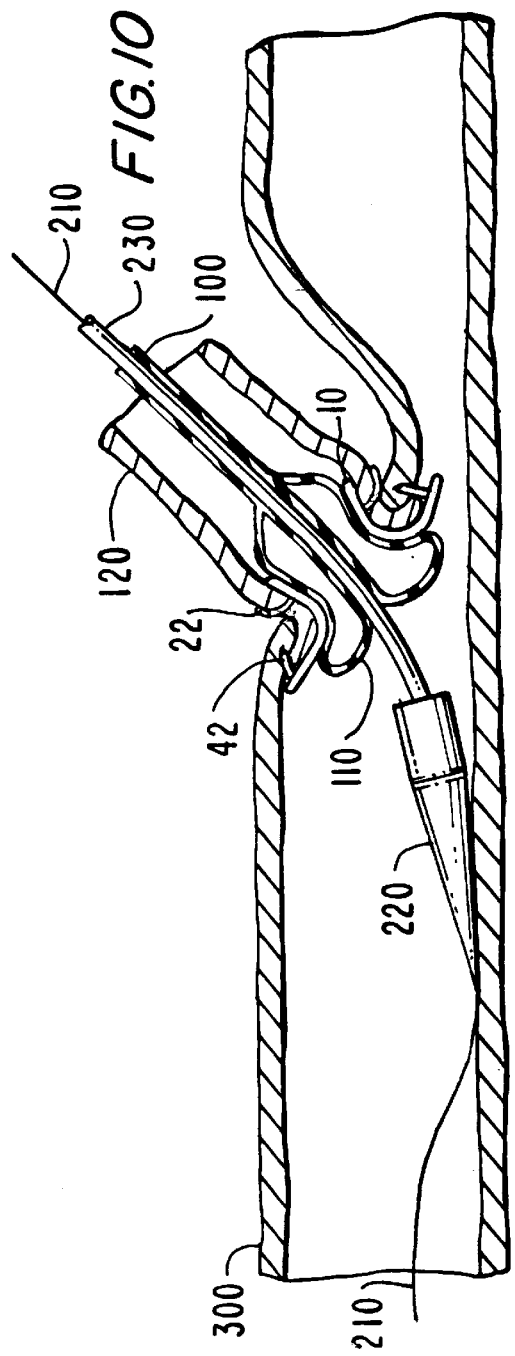

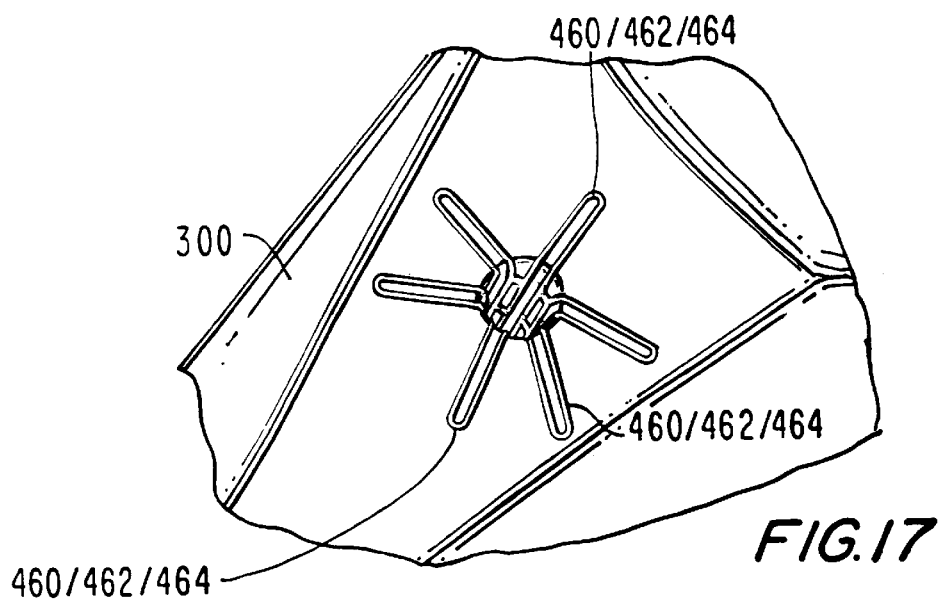
FIG. 17
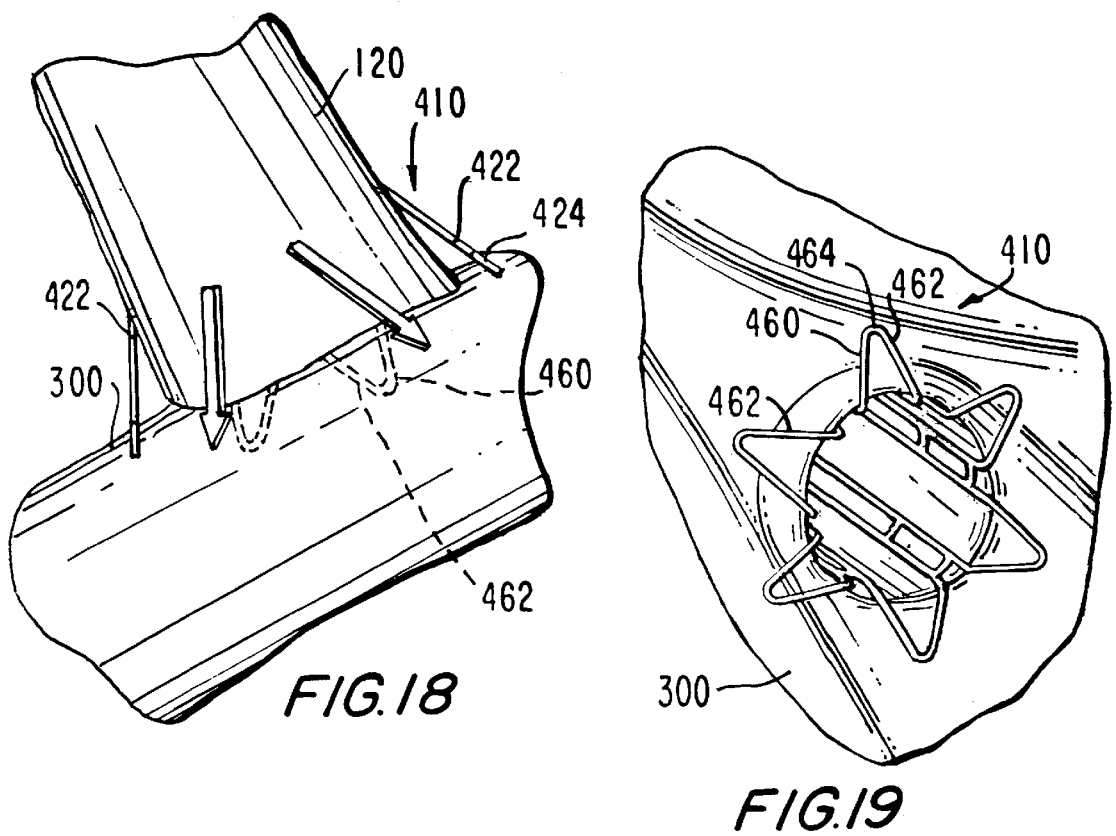
FIG. 18
FIG. 19

MEDICAL ANASTOMOSIS APPARATUS

BACKGROUND OF THE INVENTION

This invention relates to medical apparatus, and more particularly to apparatus for use in making anastomotic connections between tubular body fluid conduits in a patient.

There are many medical procedures in which it is necessary to make an anastomotic connection between two tubular body fluid conduits in a patient. An anastomotic connection (or anastomosis) is a connection which allows body fluid flow between the lumens of the two conduits that are connected, preferably without allowing body fluid to leak out of the conduits at the location of the connection. As just one example of a procedure in which an anastomosis is needed, in order to bypass an obstruction in a patient's coronary artery, a tubular graft supplied with aortic blood may be connected via an anastomosis to the contrary artery downstream from the obstruction. The anastomosis may be between the end of the graft and an aperture in the side wall of the coronary artery (a so-called end-to-side anastomosis), or the anastomosis may be between an aperture in the side wall of the graft and an aperture in the side wall of the coronary artery (a so-called side-to-side anastomosis (e.g., as in published Patent Cooperation Treaty ("PCT") patent application WO 98/16161, which is hereby incorporated by reference herein in its entirety)). The graft may be natural conduit, artificial conduit, or a combination of natural and artificial conduits. If natural conduit is used, it may be wholly or partly relocated from elsewhere in the patient (e.g., wholly relocated saphenous vein or partly relocated internal mammary artery). Alternatively, no relocation of the graft may be needed (e.g., as in above-mentioned application WO 98/16161 in which a length of vein on the heart becomes a "graft" around an obstruction in an immediately adjacent coronary artery). More than one anastomosis may be needed. For example, a second anastomosis may be needed between an upstream portion of the graft conduit and the aorta or the coronary artery upstream from the obstruction in that artery. Again, this second anastomosis may be either an end-to-side anastomosis or (as shown, for example, in above-mentioned application WO 98/16161) a side-to-side anastomosis. Alternatively, no second, upstream anastomosis may be required at all (e.g., if the graft is an only-partly-relocated internal mammary artery).

The currently most common technique for making an anastomosis is to manually suture the two tubular body fluid conduits together around an opening between them. Manual suturing is difficult and time-consuming, and the quality of the anastomosis that results is highly dependent on the skill of the person doing the suturing. In the case of coronary artery bypass procedures, one source of difficulty for suturing of an anastomosis may be motion of the heart. There is also increasing interest in procedures which are less invasive or even minimally invasive. Such procedures have potentially important advantages for patients, but they may increase the difficulty of performing manual suturing of an anastomosis by reducing or limiting access to the site within the patient at which the anastomosis must be made. Various examples of such less invasive or minimally invasive procedures are shown in above-mentioned application WO 98/16161, Goldsteen et al. U.S. Pat. No. 5,976,178, Sullivan et al. U.S. patent application Ser. No. 08/844,992, filed Apr. 23, 1997, Sullivan et al. U.S. patent application Ser. No. 08/869,808, filed Jun. 5, 1997, and Berg et al. U.S. patent application Ser. No. 09/187,364, filed Nov. 6, 1998, all of which are hereby incorporated by reference herein in their entireties.

In view of the foregoing, it is an object of this invention to provide apparatus that can be used to make anastomotic connections in lieu of manual suturing.

It is another object of the invention to provide apparatus that can be used to make anastomotic connections even though access to the site of the anastomosis may be limited or even only indirect or remote.

It is still another object of the invention to provide apparatus that can be used to make anastomotic connections without the need for a high degree of manual suturing skill.

It is yet another object of the invention to provide apparatus for making anastomotic connections that is less adversely affected than manual suturing by adjacent or nearby body motion (e.g., motion of the patient's heart).

It is still another object of this invention to provide apparatus for facilitating the making of higher quality anastomotic connections more rapidly and with more consistent results than is possible with prior art methods and apparatus such as manual suturing.

SUMMARY OF THE INVENTION

These and other objects of the invention are accomplished in accordance with the principles of the invention by providing a connector for use in making an anastomotic connection between two tubular body fluid conduits in a patient, the connector being of substantially one-piece or unitary construction which extends annularly about a central longitudinal axis. The structure of the connector includes axially spaced first and second portions, at least one of which includes members that are deflectable radially out from a remainder of the connector structure. In some embodiments both of the axially spaced first and second portions include members that are deflectable radially out from a remainder of the structure. The connector structure is annularly enlargeable, preferably by inflation of a balloon placed temporarily inside the connector. The structure of the connector preferably lends itself to formation by removal of selected material from a single unitary tube. The connector is typically made of metal which is plastically deformable (e.g., in the above-mentioned radial outward deflections and annular enlargement).

The members that are deflectable radially out from the first portion of the connector structure are configured to engage the side wall of one of the two tubular body fluid conduits that are to be connected. The members that are deflectable radially out from the second portion of the connector structure are configured to engage the side wall of the other of the two body fluid conduits that are to be connected. Alternatively, one of the two portions of the connector can be secured (preferably pre-secured) to the associated conduit by other means such as sutures. Annular expansion of the connector preferably causes the first and second portions of the connector structure to move toward one another along the central longitudinal axis of the connector, thereby causing the connector to draw the two tubular body fluid conduits together at the anastomosis between them. This helps produce an anastomosis which is fluid-tight (i.e., from which body fluid does not leak).

The connectors of this invention can be used to provide either end-to-side or side-to-side anastomoses. The connector may be first attached to one of the body fluid conduits to be connected (e.g., an end portion of a graft conduit), and then delivered along with the attached end of the first conduit to the connection point with the second conduit, where the connector is fully deployed to produce an anastomosis between the first and second conduits. Prior to full deployment the connector preferably has a relatively small circumference, which facilitates delivery and initial installation in the patient, even at relatively remote or inaccessible locations in the patient. For example, the connector can be delivered via lumens of body fluid conduits in the patient and/or relatively small-diameter instrumentation such as a cannula or laparascopic-type device. Final installation can be performed substantially solely by inflation of a balloon temporarily disposed in the connector. No direct manipulation of the connector may be needed. All of these attributes facilitate use of the connector at remote or inaccessible locations in the patient. The connector therefore lends itself to use in less invasive or minimally invasive procedures.

Instrumentation for facilitating installation of the connector through the side wall of a body fluid conduit is also disclosed. This instrumentation has a gradually tapered distal nose portion with an outer surface that is free of features that could snag on the side wall of the body fluid conduit to be penetrated by the nose portion. At least the portion of the connector that must pass through the body fluid conduit side wall is completely covered by the instrumentation until that portion of the connector is through the side wall. These features of the instrumentation help it penetrate the body fluid conduit side wall with no snagging and with minimal trauma. Thereafter the distal nose portion can be shifted distally relative to the connector to expose the connector in position through the side wall. Other parts of the instrumentation (e.g., an inflatable balloon) can then be operated to complete the deployment of the connector.

Further features of the invention, its nature and various advantages will be more apparent from the accompanying drawings and the following detailed description of the preferred embodiments.

BRIEF DESCRIPTION OF THE DRAWINGS

FIG. 7 is a simplified sectional view of the structure of FIG. 6 with additional illustrative apparatus shown for use in delivering and deploying the FIG. 6 structure in a patient in accordance with the invention.

FIG. 8 is a simplified elevational view, partly in section, showing an early stage in use of the FIG. 7 apparatus in accordance with the invention.

FIG. 9 is a view similar to FIG. 8, but with more elements shown in section, and showing a later stage in use of the FIG. 7 apparatus in accordance with the invention.

FIG. 10 is a view similar to FIG. 9 showing a still later stage in use of the FIG. 7 apparatus in accordance with the invention.

FIG. 17 is another view, generally similar to FIG. 16, showing an even later stage in use of the elements shown in FIG. 16.

FIG. 18 is a simplified perspective view of a completed anastomosis including the connector of FIG. 12.

FIG. 19 is another view, partly in section, of the anastomosis of FIG. 18.

DETAILED DESCRIPTION OF THE PREFERRED EMBODIMENTS

Figure 1:
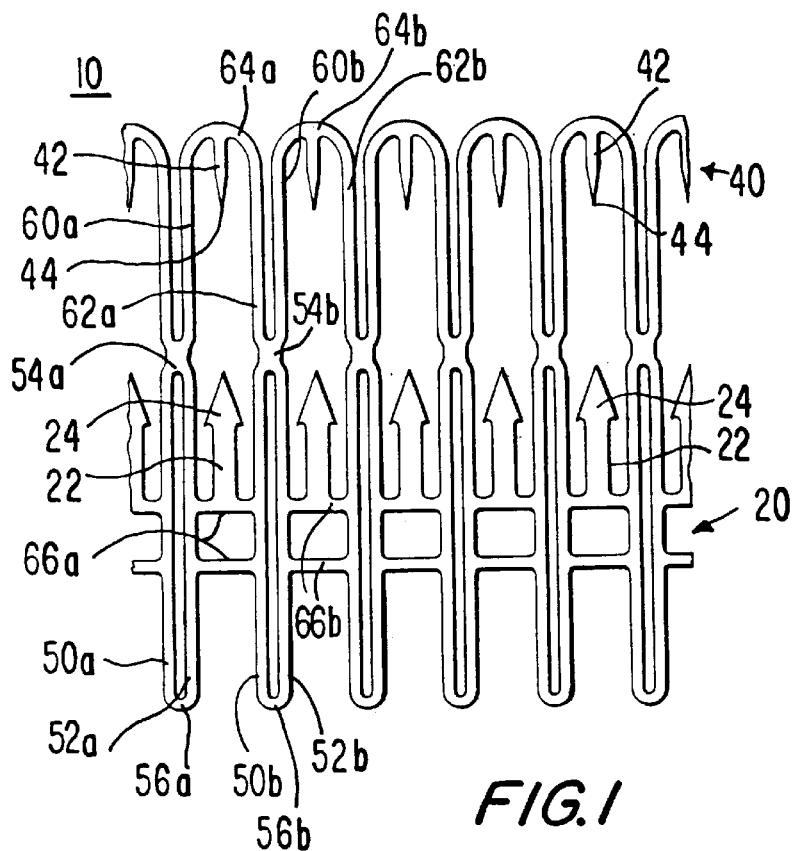
FIG. 1 is a simplified planar development of the structure of an illustrative embodiment of a connector constructed in accordance with this invention.
Figure 2:
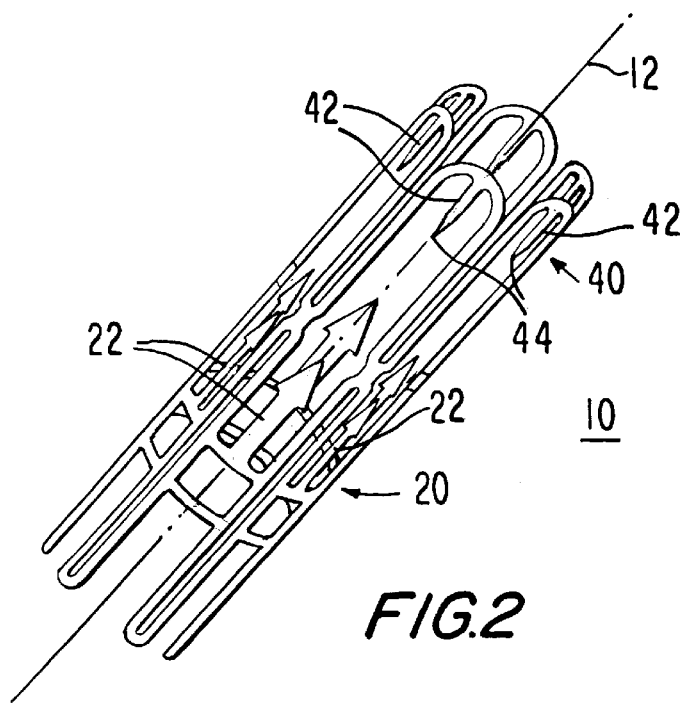
FIG. 2 is a simplified perspective view of the actual structure of the connector which is shown in planar development in FIG. 1.

FIG. 1 shows a planar development of what is actually an integral, one-piece (unitary), annular structure 10. In particular, the left and right edges of the structure shown in FIG. 1 are actually joined to and integral with one another. Thus the actual structure is as shown in FIG. 2, although FIG. 1 is useful to more clearly reveal the details of various features of the structure. A central longitudinal axis 12 about which structure 10 is annular is shown in FIG. 2.

An illustrative material for structure 10 is 304 stainless steel. Other examples of suitable materials include tantalum, tungsten, platinum, and nitinol. Structure 10 may be advantageously produced by starting with a single, unitary metal tube and removing selected material until only the structure shown in FIG. 2 remains. For example, laser cutting may be used to remove material from the starting tube in order to produce structure 10. Although connectors 10 can be made in various sizes for various uses, a typical connector has an initial outside diameter in the range from about 0.040 to about 0.065 inches, an initial length of about 4.0 mm, and a material thickness-of about 0.004 inches.

Connector 10 may be described as including axially spaced first and second portions 20 and 40, respectively.

Figure 3:
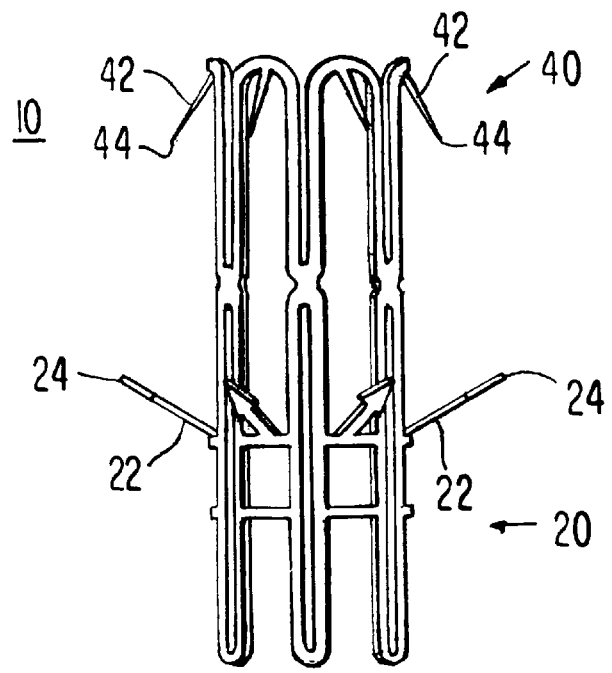
FIG. 3 is a simplified elevational view of the FIG. 2 structure after some further processing in accordance with the invention.

First portion 20 includes a plurality of annularly spaced members 22 that in this case have free end portions 24 that are sharply pointed and that point toward second portion 40. Each of members 22 is deflectable radially out from the remainder of structure 10 as shown, for example, in FIG. 3. This outward deflection is preferably at least partly plastic.

Second portion 40 also includes a plurality of annularly spaced members 42 that in this case have free end portions 44 that are sharply pointed and that point toward first portion 20. Each of members 42 is deflectable radially out from the remainder of structure 10 as shown, for example, in FIG. 3. Again, this outward deflection is preferably at least partly plastic.

The above-mentioned outward deflection of elements 22 and 42 can be produced by putting the connector on a mandrel and prying elements 22 and 42 radially outward.

Figure 4:
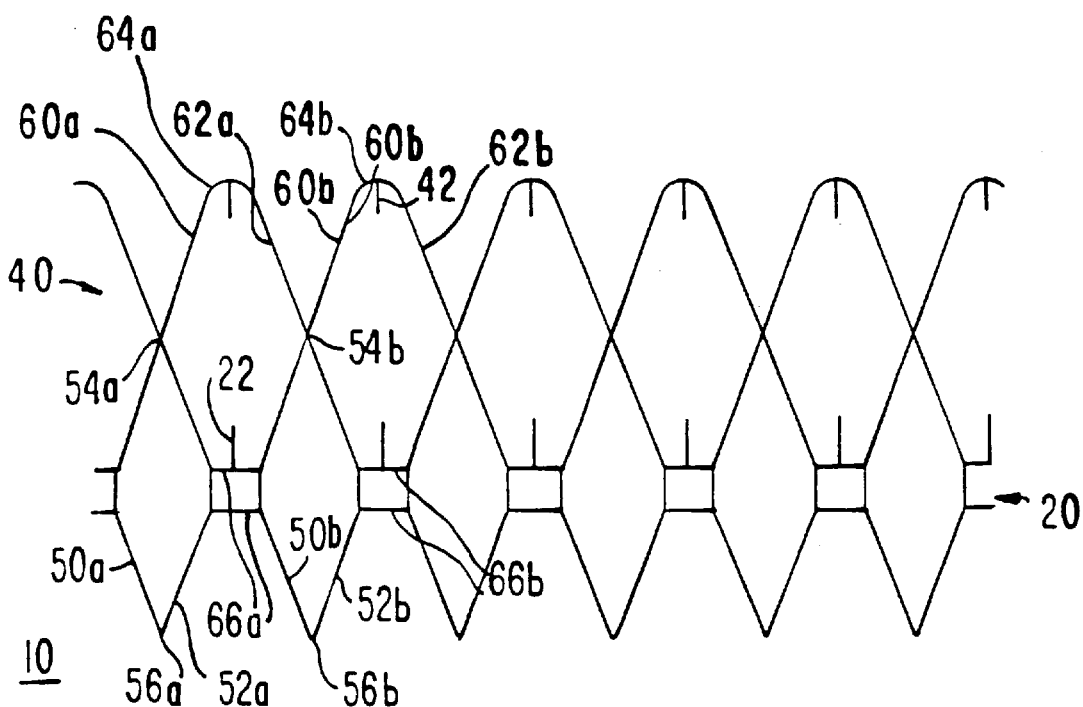
FIG. 4 is a simplified planar development of the structure of FIGS. 1–3 showing that structure's capacity for annular enlargement in accordance with the invention.
Figure 11:
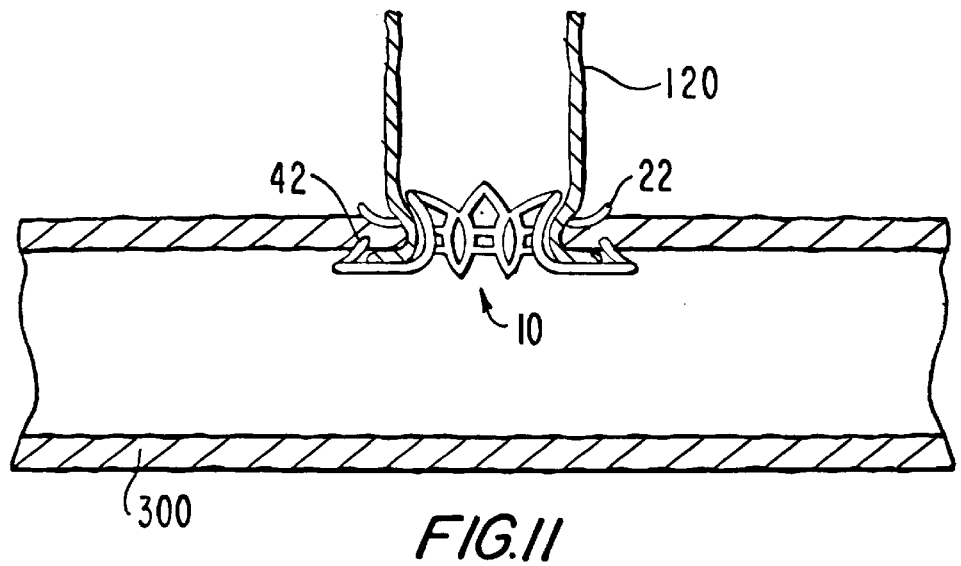
FIG. 11 is a view similar to FIG. 10 showing the end result of using the FIG. 7 apparatus in accordance with the invention.

Connector 10 is formed in such a way that it is annularly enlargeable (e.g., by inflation of a balloon that is temporarily disposed inside the connector). The annularly expanded condition of connector 10 is shown in FIGS. 4, 10, and 11. The annular expandability of connector 10 is provided by making the connector with a plurality of annularly adjacent, annularly enlargeable cells. For example, a typical cell includes annularly spaced, but adjacent, longitudinal members 50a and 52a. The axially spaced ends of this pair of members are connected to one another at 54a and 56a. The next annularly adjacent similar cell includes elements 50b, 52b, 54b, and 56b. Annularly adjacent ones of these cells are connected to one another (e.g., as at 66a) at locations which are axially medial to their axial end connections 54 and 56. In this way structure 10 is annularly enlargeable by annularly enlarging each of the above-mentioned cells (see FIG. 4).

In addition to the cells that are described above, structure 10 includes other, similarly annularly expandable cells that are axially and annularly offset from the first-described cells. A representative one of these other cells includes annularly adjacent longitudinal members 60a and 62a, the axially spaced ends of which are connected at 64a and 66a. (It should be noted that part of member 60a is common with part of member 52a, and part of member 62a is common with part of member 50b.) The next annularly adjacent cell of this kind includes components 60b, 62b, 64b, and 66b. Annularly adjacent cells of this kind are connected to one another at locations like 54b, which are axially medial the axial endpoints 64 and 66 of those cells. Thus again the structure is annularly enlargeable by annularly enlarging these cells as shown, for example in FIG. 4.

It will be appreciated that as structure 10 annularly enlarges, it generally axially shortens. In other words, as cells 50/52/54/56 and 60/62/64/66 widen in the annular direction, they shorten in the axial direction. Thus annular enlargement of structure 10 decreases the axial spacing between portions 20 and 40, and more particularly decreases the axial spacing between member 22, on the one hand, and members 42, on the other hand.

Figure 5:
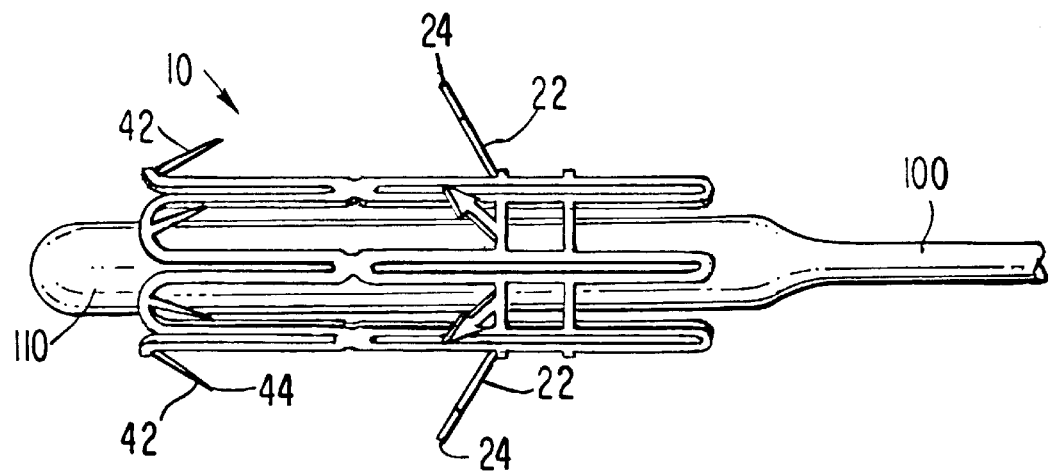
FIG. 5 is a simplified elevational view of the structure of FIG. 3 with some additional structure in accordance with the invention.

A typical use of connector 10 is, in a coronary artery bypass procedure, to provide an anastomosis between an axial end portion of a tubular graft conduit and an aperture in a side wall of a coronary artery. For this kind of use connector 10 may be loaded on an uninflated balloon 110 near the distal end of a balloon catheter 100 as shown in FIG. 5. In other words, connector 10 and catheter 100 are assembled so that connector 10 extends annularly around uninflated balloon 110.

Figure 6:
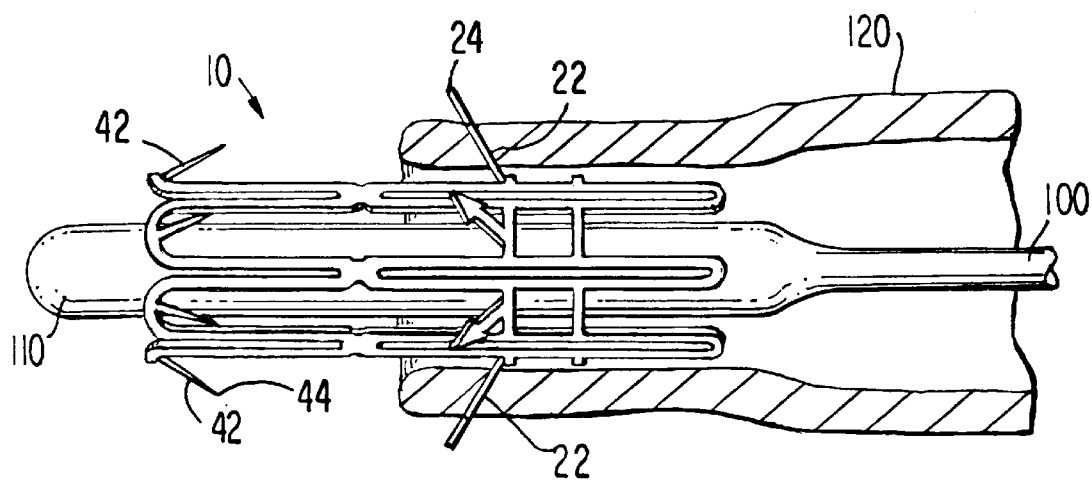
FIG. 6 is a simplified elevational view, partly in section, of the structure of FIG. 5 with still more additional structure in accordance with the invention.

Graft conduit 120 is then placed annularly around the first portion 20 of connector 10 and the adjacent portion of catheter 100 as shown in FIG. 6. Graft conduit may be natural body tissue (e.g., a length of the patient's saphenous vein harvested for use as a graft, a partly severed internal mammary artery, etc.), an artificial graft (e.g., as shown in Goldsteen et al. U.S. Pat. No. 5,976,178, or published PCT WO 98/19832, both of which are hereby incorporated by reference herein in their entireties), or a combination of natural and artificial conduits (e.g., a length of natural conduit disposed substantially concentrically inside a length of artificial conduit). Graft conduit 120 is placed on assembly 10/100 so that radially outwardly deflected members 22 penetrate and pass through the side wall of the graft conduit (e.g., as a result of compressing the graft against the fingers, thereby forcing the fingers to pierce through the graft wall). The sharpened free ends of members 22 facilitate penetration of conduit 120 by members 22. The blunt rear surfaces of enlarged free end portions 24 resist withdrawal of members 22 from conduit 120 after members 22 have penetrated the conduit. The graft may be additionally or alternatively directly sutured to the connector body. If the alternative of suturing graft 120 to the connector is used, then the first portion 20 of the connector may not need radially outwardly deflectable members 22 for engagement of the graft conduit.

As an alternative to securing graft 120 to connector 10 after balloon 110 has been associated with the connector, balloon 110 may be installed in connector 10 after the graft has been secured to the connector.

Illustrative apparatus 200 for delivering connector 10 and graft 120 to a location in a patient requiring a graft and an anastomosis, and for then deploying the connector and graft, is shown in FIG. 7. Apparatus 200 includes an optional guide wire 210, which may be first installed in the patient along the route that the remainder of the apparatus is later to follow to reach the desired location in the patient. The remainder of the apparatus is then slid into the patient along guide wire 210. Alternatively, guide wire 210 may be omitted, or a leading guide member (e.g., a wire) may be fixedly mounted on the distal (leftward in FIG. 2) end of the remainder of the apparatus. The wire allows precise tracking of the nose cone 220 and delivery system 200 into a patient's body fluid conduit (e.g., a coronary artery 300 as shown in FIGS. 8–10 and described below).

Apparatus 200 includes a gradually tapered distal nose portion or dilator 220 which extends annularly around a central, longitudinally extending, guide wire lumen 222. Distal nose portion 220 has a substantially conical outer surface with a cone angle A, which is preferably less than about 15° (e.g., in the range from about 5° to about 15°, more preferably in the range from about 5° to about 10°). Such gradual tapering of nose portion 220 is desirable to enable nose portion to gradually enlarge an aperture in a side wall of a body fluid conduit to which graft 120 is to be connected without snagging on that conduit side wall. This geometry allows optimal passage across a body conduit wall (e.g., a coronary artery wall as shown in FIG. 8 and described below) with minimal wall damage, with minimal force being required, and with no catching or snagging on the wall. Distal nose portion 220 may have cutting edges to further facilitate entry through a body fluid conduit side wall.

Distal nose portion 220 is connected to tube 230, which extends proximally from the nose portion annularly around guide wire 210. Thus the lumen of tube 230 constitutes a proximal continuation of guide wire lumen 222. Tube 230 may be made of stainless steel hypotube, which allows the depicted apparatus to be pushed or pulled axially along guide wire 210.

A proximal portion of distal nose portion 220 is hollowed out as indicated at 224 to receive balloon 110, connector 10, and a distal portion of graft 120 substantially coaxially around a medial portion of tube 230. For this arrangement balloon 110 is provided as a hollow annulus at or near the distal end of hollow tubular member 100. The side wall of tube 100 may include a separate lumen (not shown but conventional for balloon catheters) through which pressurized inflation fluid may be supplied from a proximal region of the apparatus to balloon 110. Elements 100 and 110 are slidable axially along the outer surface of tube 230. Insertion of elements 10, 110, and 120 (FIG. 6) into the annular recess 224 in distal nose portion 220 deflects the radially outermost portions of members 22 back over graft 120 as shown in FIG. 7. Tube 240, disposed substantially coaxially around element 100 inside graft 120 so that its distal end bears against members 22, may be used to help load elements 10, 110, and 120 into recess 224, and also to hold connector 10 in place in recess 224 during delivery of the connector to the anastomosis site in the patient.

FIG. 8 shows a typical use of apparatus 200 to deliver graft 120 for connection to an aperture in a side wall of a patient's tubular body conduit 300 (e.g., a coronary artery requiring a bypass graft). Guide wire 210 is first installed through a small aperture in the side wall of the conduit. The natural elastic recoil of the conduit 300 side wall seals the aperture around the guide wire so that there is little or no body fluid (e.g., blood) leakage out of the conduit via the aperture. The tapered distal nose portion 220 of apparatus 200 is then gradually forced into the aperture (e.g., by using tube 230 to push portion 220 distally into the aperture) to dilate the aperture. The natural elastic recoil of the conduit 300 side wall tissue continues to keep the aperture sealed or substantially sealed around portion 220.

When distal nose portion 220 has been pushed far enough into the aperture in the side wall of conduit 300 so that connector 10 is part way through the aperture, further distal motion of elements 10, 100, 110, and 120 can be stopped (e.g., by holding a proximal portion of element 100 stationary). Tube 240 is then pulled proximally out of the patient. Thereafter, distal nose portion 220 is pushed farther into conduit 300 (e.g., by continuing to push distally on a proximal portion of element 230). This causes distal nose portion 220 to separate from connector 10, thereby exposing the connector and leaving it in the aperture through the conduit 300 side wall as shown in FIG. 9.

The next step in use of apparatus 200 is to inflate balloon 110 as shown in FIG. 10. The balloon is typically sized to a specific anastomosis size (e.g., 3 millimeters diameter, 4 millimeters diameter, etc.). Inflation of the balloon forces connector 10 to annularly enlarge by enlarging cells 50/52/54/56 and 60/62/64/66 in the annular direction. In addition, the portions of members 60 and 62 that are adjacent to elements 64 (as well as elements 64 and 42) are deflected radially out beyond other portions of the connector inside the side wall of conduit 300, thereby causing the extreme distal end of graft 120 to similarly flare out inside that side wall. This outward flaring of portions of connector 10 and graft 120 helps secure the connector and graft to the side wall of conduit 300, and also helps seal the graft to the conduit. The axial shortening of connector 10 that accompanies annular enlargement ensures that graft 120 is drawn into secure and fluid-tight engagement with conduit 300. The free ends of members 42 preferably penetrate the side wall of conduit 300 to further secure connector 10 and graft 120 in the aperture in the side wall. Members 50, 52, 56, and 24 may also flare out somewhat outside the side wall of graft 300 to help ensure that graft 120 remains open where it connects to conduit 300. Assuming that the connector is approximately properly positioned relative to the side wall of conduit 300 prior to inflation of balloon 110, the connector is effectively self-centering on the conduit 300 side wall as the balloon is inflated.

The next step in use of apparatus 200 is to deflate balloon 110 and withdraw all of elements 100, 110, 210, 220, and 230 (e.g., by pulling them proximally out of graft 120). This leaves the axial end portion of graft 120 connected to the side wall of conduit 300 by annularly enlarged connector 10 as shown in FIG. 11. In particular, in this example connector 10 provides an end-to-side anastomosis between graft 120 and conduit 300. Body fluid from graft 120 is able to flow into conduit 300 via this connection. Connector 10 presses graft 120 radially outward against the aperture through the side wall of conduit 300 all the way around that aperture, thereby preventing body fluid from leaking out of conduits 120 and 300. Connector 10 also prevents the end of conduit 120 from pulling out of the side wall of conduit 300.

Figure 12:
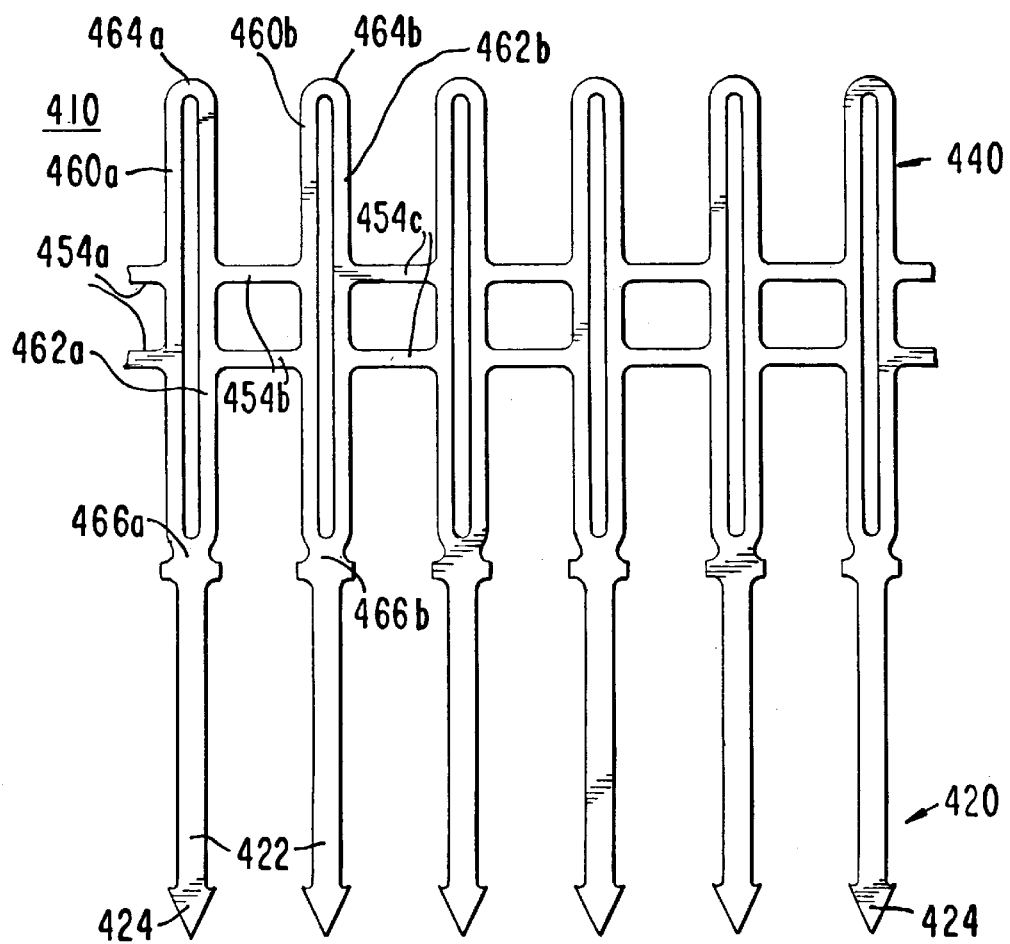
FIG. 12 is a view similar to FIG. 1 for another illustrative embodiment of a connector constructed in accordance with the invention.

Another illustrative embodiment of a connector 410 in accordance with this invention is shown (in simplified planar development) in FIG. 12. Again, although connector 410 can be made in various sizes for various uses, a typical initial length of connector 410 is about 4.0 mm, and a typical initial outside diameter is in the range from about 0.040 to about 0.065 inches. A typical shaft length for members 422 is about 0.0539 inches, and a typical shaft width for those members is about 0.0050 inches. As in the case of connector 10, connector 410 may be cut from a single integral tube. A typical thickness for the material of connector 410 is about 0.004 inches. Suitable materials for connector 410 include stainless steel, tantalum, tungsten, platinum, and nitinol.

Connector 410 may be described as including axially spaced first and second portions 420 and 440, respectively. First portion 420 includes a plurality of annularly spaced first members 422 having free end portions 424 that initially point axially away from second portion 440. However, members 422 are deflectable radially out from other parts of the connector, and, if desired, free end portions 424 can be curved back so that they point toward second portion 440 (see FIG. 15).

The first portion 420 of connector 410 may also be said to include the lower portions (below members 454) of cells, each of which includes one member 460, one member 462, one member 464, and one member 466. For example, the left-most cell shown in FIG. 12 includes substantially parallel members 460a and 462a joined at their axially spaced ends by members 464a and 466a. Annularly adjacent cells are joined by members 454 at points that are axially medial their axial ends. For example, the cell that includes member 462a is joined to the cell that includes member 460b by members 454b. The portions of members 460 and 462 below members 454 are also deflectable radially out from other portions of the connector.

The second portion 440 of connector 410 may be said to include the portions of members 460 and 462 above members 454. These portions of members 460 and 462 are also deflectable radially out (as loops 460/462/464) from other portions of the connector. If desired, loops 460/462/464 could also have fingers or barbs on them like members 42 in the embodiment of FIGS. 1–11.

Figure 13:
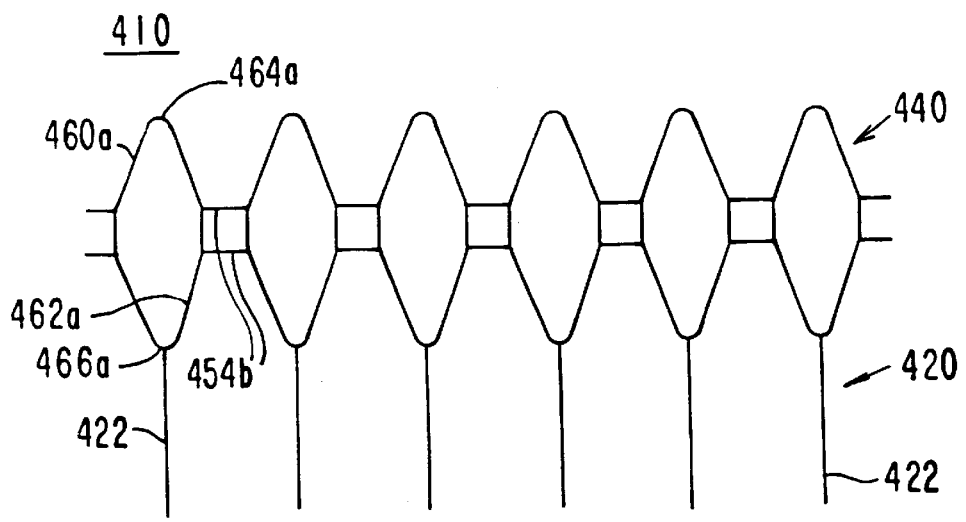
FIG. 13 is a view similar to FIG. 4, but for the embodiment of FIG. 12.

Connector 410 is annularly enlargeable by deforming members 460 and 462 to enlarge each of the above-described cells in the annular direction as shown in greatly simplified form in FIG. 13.

Figure 14:
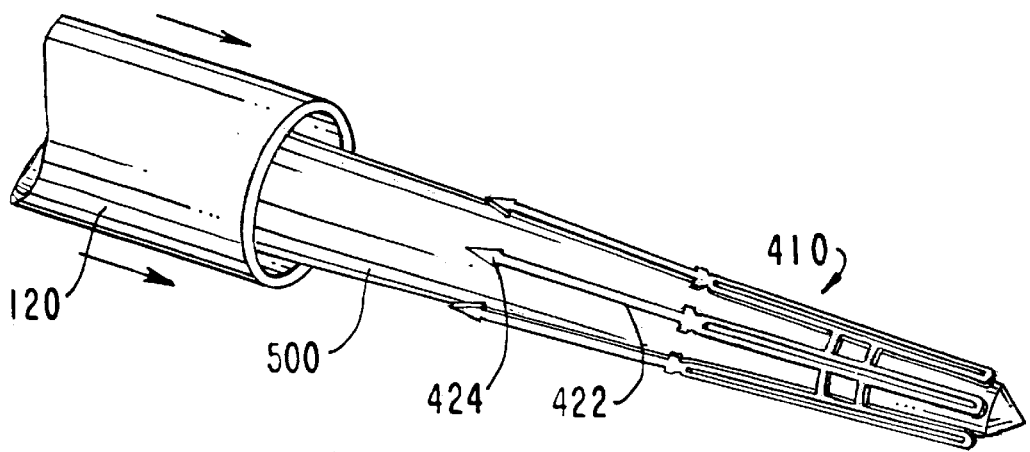
FIG. 14 is a simplified perspective view showing the connector of FIG. 12 with other elements in accordance with the invention.
Figure 15:
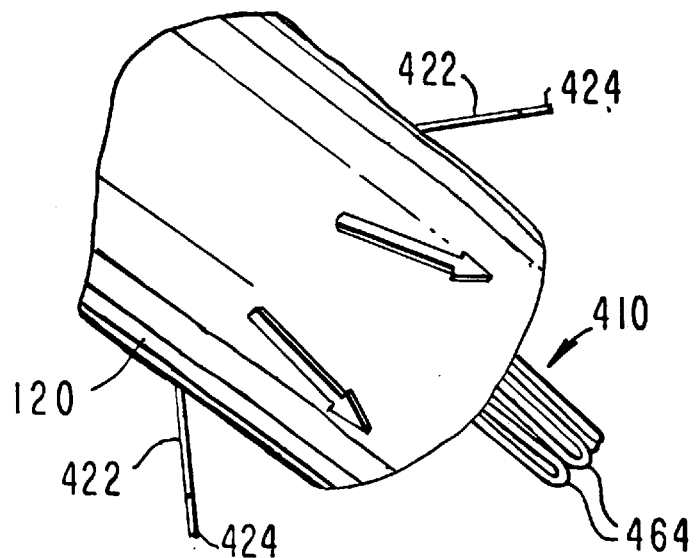
FIG. 15 is another simplified perspective of a later stage in use of some of the elements shown in FIG. 14.

FIG. 14 shows an illustrative embodiment of tooling 500 that can be used to facilitate attachment of a graft conduit 120 to connector 410. Tooling 500 includes a mandrel with a conical end portion, the pointed free end of which is small enough to fit axially into connector 410 in its initial relatively small annular size. As connector 410 is forced farther onto the conical end portion of mandrel 500, the cone of the mandrel begins to deflect members 422 radially out from other portions of the connector. Graft conduit 120 can be placed around mandrel 500 and shifted axially toward connector 410 until an axial end portion of conduit 120 axially overlaps outwardly deflected members 422. The free end portions of members 422 can then be pried out through the side wall of conduit 120 as shown in FIG. 15 to secure connector 410 to conduit 120. Mandrel 500 can be pulled proximally out of graft 120 and connector 410 at any suitable time. Use of mandrel 500 in this way helps ensure that members 422 penetrate the side wall of conduit 120 substantially equidistantly in the annular direction around the conduit. This helps avoid excessive stretching of any angular segment of graft 120 when connector 410 is subsequently expanded by balloon 110.

Figure 16:
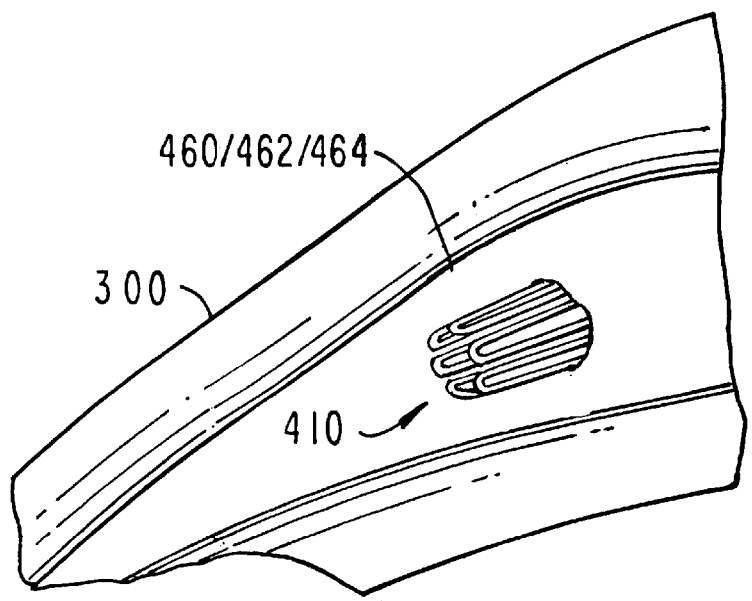
FIG. 16 is another simplified perspective view, partly in section, of a still later stage in use of the elements shown in FIG. 15.

After connector 410 has been attached to graft 120 as shown in FIG. 15, an inflatable balloon like balloon 110 (with tube 100) can be inserted into the connector in a manner similar to what is shown in FIG. 6. Elements 100, 110, 120, and 410 can then be loaded into apparatus like 200 in a manner similar to what is shown in FIG. 7 (except that in this case the free ends 424 of members 422 will typically point in the distal direction rather than in the proximal direction as is true for the free ends 24 of members 22 in FIG. 7). Apparatus 200 can then be used to install connector 410 and graft 120 in a patient in a manner similar to the installation shown in FIGS. 8–11. FIG. 16 shows the second portion 440 after it has been conveyed through the side wall of conduit 300 by apparatus 200 and apparatus 200 has been shifted distally farther into conduit 300 to expose the connector. FIG. 17 shows second portion loops 460/462/464 deployed (radially outwardly deflected), but the remainder of the connector not yet annularly expanded. A shaped balloon or dual balloon system may be utilized to achieve this. For example, one of two axially adjacent balloons may be used to help form distal retention fingers 460/462/464 as shown in FIG. 17. The second of the two balloons is thereafter used to annularly expand the remainder of the connector and the anastomosis opening. Alternatively, a single "bulbous" shaped balloon may be used to produce a temporary intermediate condition like that shown in FIG. 17, and to then annularly enlarge the remainder of the connector and the anastomosis opening. As still another possibility the distal retention fingers 460/462/464 may be self-actuating (i.e., spring-biased) and not require balloon assist to spring out to the condition shown in FIG. 17. For example, distal retention fingers 460/462/464 may be preformed to deflect radially outward in a manner similar to the radially outward preform that is given to elements 22 and 42 in FIG. 3.

The final anastomosis employing connector 410 is shown in FIGS. 18 and 19. In particular, as shown in FIGS. 18 and 19 connector 410 has been annularly expanded by enlargement of the cells 460/462/464/466 in the annular direction. The portions of members 460 and 462 that comprise portion 440 of the connector have been deflected radially out from other portions of the connector inside conduit 300, thereby functioning to secure connector 410 and graft 120 to conduit 300. Members 422 are deflected radially out from other portions of the connector and pass through the axial end portion of graft 120. The free end portions of members 422 point toward the second portion 440 of the connector, thereby ensuring that the end of graft 120 cannot slip away from its body-fluid-sealing abutment with the side wall of conduit 300. The annularly expanded medial portion of connector 410 holds open the aperture in the side wall of conduit 300, as well as the attached end of graft 120, thereby ensuring unobstructed body fluid flow through the anastomosis between conduits 120 and 300.

Figure 24:
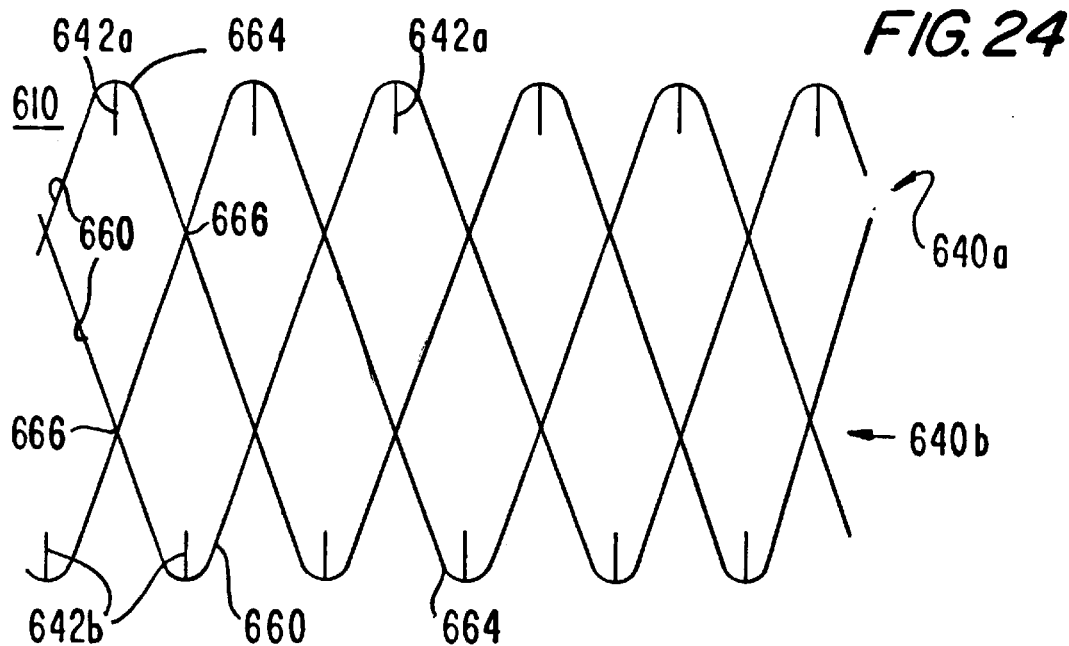
FIG. 24 is a view similar to FIG. 4 for still another illustrative embodiment of a connector constructed in accordance with the invention.
Figure 25:
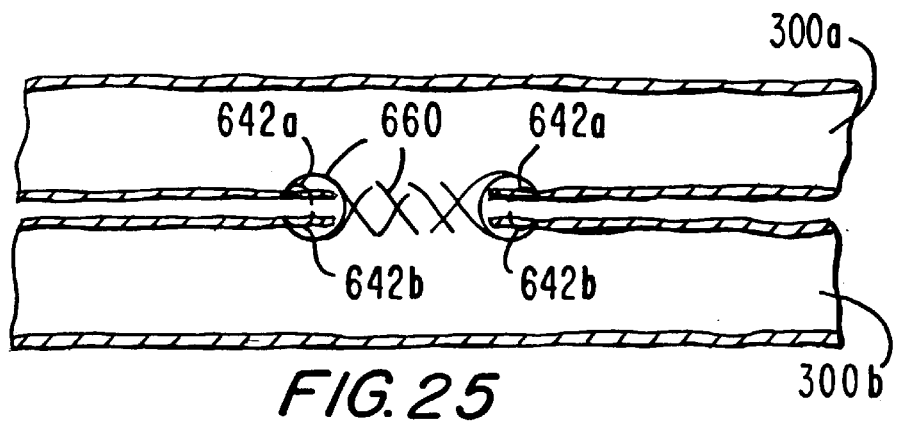
FIG. 25 is a view similar to FIG. 11 for a completed anastomosis employing a connector of the type shown in FIG. 24.

Still another illustrative embodiment of a connector 610 in accordance with this invention is shown in greatly simplified, annularly expanded, planar development in FIG. 24. Connector 610 is configured for use in performing a side-to-side anastomosis between two body fluid conduits 300a and 300b as shown in FIG. 25. Connector 610 has a construction like two portions 40 of connector 10 connected together. Thus members 642a and 642b are constructed and operate like members 42 in connector 10. Similarly, members 660 are constructed and operate generally like members 60 and 62 in connector 10, and elements 664 and 666 are constructed and operate generally like elements 64 and 66, respectively, in connector 10.

Connector 610, in an initially relatively small annular size and mounted on a balloon, is insertable through adjacent apertures in the side walls of body fluid conduits 300a and 300b. For example, apparatus like 200 can be used to deliver connector 610 to such a site via the lumen of one of conduits 300 and to then position the connector so that it spans both conduits. Apparatus 200 is then shifted relative to connector 610 in a manner generally similar to FIG. 9 to expose the connector. The balloon 110 associated with the connector is then inflated to annularly enlarge the connector to the condition shown in FIG. 25. In particular, this annular expansion causes members 642a to penetrate the side wall of conduit 300a annularly around the anastomotic opening, and also causes members 642b to penetrate the side wall of conduit 300b annularly around the anastomotic opening. As with the other connectors of this invention, annular enlargement of connector 610 is accompanied by axial shortening, which helps to draw the side walls of conduits 300a and 300b together annularly around the connector, thereby providing the desired fluid-tight anastomosis between the conduits. When the anastomosis is thus complete, the balloon inside the connector is deflated and all the apparatus is withdrawn through the anastomosis.

Figure 23:
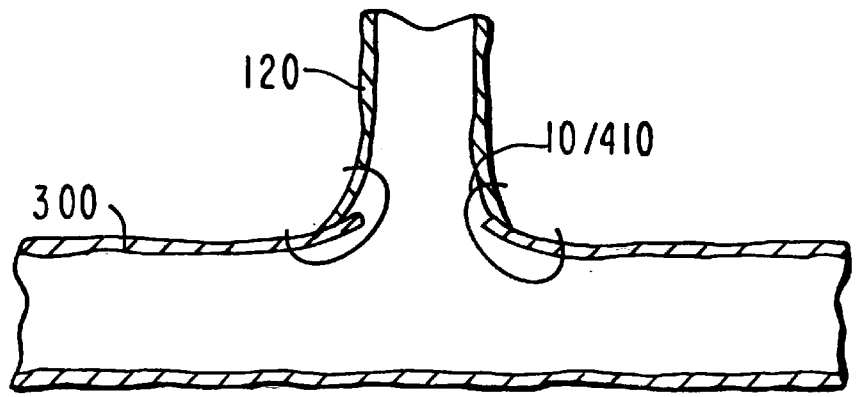
FIG. 23 is a simplified sectional view of an alternative finished anastomosis in accordance with the invention.

It will be understood that the foregoing is only illustrative of the principles of this invention, and that various modifications can be made by those skilled in the art without departing from the scope and spirit of the invention. For example, the number and shape of the annularly enlargeable connector cells can be different from what is shown in the drawings herein. The number of axially adjacent rows of annularly enlargeable cells can be different from the numbers of such rows that are shown herein (i.e., two rows of cells in the case of connectors 10 and 610 or one row of cells in the case of connector 410). For example, a connector may have three, four, or more rows of cells. The cells may have any of many forms, depending on the desired degree of expansion and final radial strength. The number of cells, the number of rows of cells, the size of the cells, and the geometry of the cells can all be selected to control the expansion, strength, and sizing of the finished connector. The number and shape of the radially outwardly deflectable connector members can also differ from what is shown herein. Techniques and apparatus different from what is shown and described herein can be used for attaching a connector of this invention to a graft conduit and/or installing the connector in a patient. Instead of the extreme end of graft 120 being inside conduit 300, the connector of this invention may be configured to secure the end of the graft 120 against the outside of the side wall of conduit 300 in an end-to-side anastomosis as shown in FIG. 23. The nose cone 220 of apparatus 200 may not need to cover the proximal fingers 22 or 422 of the connector. Instead, the proximal fingers can extend to an outer circumference which is larger than the outer circumference of nose cone 220. This allows the proximal fingers to be used as a stop which prevents the connector from going too far through the aperture in the side wall of conduit 300. In other words, the radially outer ends of proximal fingers 22 or 422 come into contact with the outer surface of the side wall of conduit 300 and thereby stop the connector from going any farther into that conduit.

Although considerable variation in the connectors of this invention is thus possible and contemplated, in general such connectors comprise a unitary structure disposed annularly about a longitudinal axis (e.g., axis 12 in FIG. 2). The connector structure generally has axially spaced first and second portions (e.g., 20 and 40, 420 and 440, or 640a and 640b in the depicted illustrative embodiments). The first portion generally has a plurality of annularly spaced first members that are deflectable radially out from a remainder or other generally axially medial portion of the structure. For example, in the illustrative embodiment shown in FIGS. 1–11 these first members include elements 22. In the illustrative embodiment shown in FIGS. 12–19 these first members include elements 422. In the illustrative embodiment shown in FIGS. 24 and 25 these first members include elements 642a. The second portion may also have a plurality of annularly spaced second members that are deflectable radially out from a remainder or other generally axially medial portion of the structure. For example, in the illustrative embodiment shown in FIGS. 1–11 these second members include elements 44 and (later in use of the connector) the portions of elements 60 and 62 that are above elements 54 in FIG. 1. In the illustrative embodiment shown in FIGS. 12–19 the second members include U-shaped structures that are the portions of elements 460, 462, and 464 above elements 454 in FIG. 12. In the illustrative embodiment shown in FIGS. 24 and 25 these second members include members 642b. Also, in general, the connector structures of this invention are annularly enlargeable. For example, in the illustrative embodiment shown in FIGS. 1–11 the connector is annularly enlargeable by enlarging cells 50/52/54/56 and 60/62/64/66 in the annular direction as shown, e.g., in FIG. 4. Similarly, in the illustrative embodiment shown in FIGS. 12–19 the connector is annularly enlargeable by enlarging cells 460/462/464/466 in the annular direction as shown, e.g., in FIG. 13. And in the embodiment shown in FIGS. 24 and 25 the connector is annularly enlargeable by enlarging cells 660/664/666 in the annular direction.

It will be appreciated that, in general, the structure of the connectors of this invention is such that radial enlargement of the connector reduces the axial spacing between the above-mentioned first and second members. This helps the connector draw together in a fluid-tight way the two body fluid conduits that are to be connected by the connector. In the embodiment shown in FIGS. 1–11, for example, annular enlargement of cells 60/62/64/66 causes a decrease in the axial spacing between members 22, on the one hand, and members 42, on the other hand. Similarly, in the embodiment shown in FIGS. 12–19 annular enlargement of cells 460/462/464/466 causes a decrease in the axial spacing between members 422, on the one hand, and the portions of elements 460 and 462 above elements 454 in FIG. 12, on the other hand. And in the embodiment shown in FIGS. 24 and 25 annular enlargement of the connector decreases the axial spacing between members 642a, on the one hand, and members 642b, on the other hand. The above-described axial shortening of the connector advantageously applies compressive forces (for sealing) to the body fluid conduits being connected.

In general, most of the deformation of the connectors of this invention is preferably plastic strain and therefore permanent. The deformation thus referred to includes both the above-described radially outward deflection of members like 22, 42, 422, 642, etc., and the above-described radial enlargement of the connector.

The radially outwardly deflectable members or portions of the connector may be barbs, hooks, spikes, loops, or suture rings.

The connectors of this invention may be constructed so that different portions of the connector annularly enlarge in response to different amounts of applied annular enlargement force. For example, in the embodiment shown in FIGS. 1–11, the portions of the structure above elements 54 in FIG. 1 may be made so that they are less resistant to inflation of a balloon 110 inside the connector than portions of the structure below elements 54 in FIG. 1. In an application of the type shown in FIGS. 1–11 this causes these less resistant portions to annularly enlarge by deflecting radially out inside conduit 300 before the remainder of the connector begins to significantly annularly enlarge. This early response of the less resistant portions inside conduit 300 may help to ensure that the connector does not slip out of engagement with conduit 300 during annular enlargement of the connector. This technique of making different portions of the connector with different strengths can be used to provide any sequence or phasing of annular enlargement of various portions of the connector. Alternatively or additionally, the connector can be shaped, molded, or phased in any desired way by providing a balloon structure 110 which is shaped, molded, or phased in that way. For example, balloon structure 110 may comprise two or more separately inflatable balloons of the same or different inflated circumferential size. Two such balloons may be axially displaced from one another inside the connector so that axially different portions of the connector can be annularly enlarged at different times and/or by different amounts.

Figure 20:
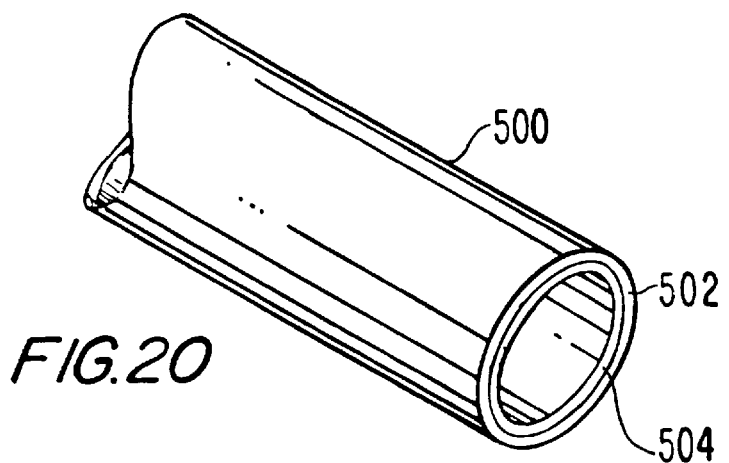
FIG. 20 is a simplified perspective view of an illustrative embodiment of a starting structure for use in making connectors in accordance with the vention.

Radiologically (e.g., x-ray) viewable markers can be used anywhere on the connectors and/or delivery apparatus (e.g., 200) of this invention to facilitate radiologic observation of the proper placement and deployment of a connector in a patient if the connector-utilizing procedure is such that more direct visual observation is not possible or sufficient. One way to enhance the radiologic viewability of connectors in accordance with this invention is to make them from clad tubing. Clad tubing has two (or more) substantially concentric layers of metal, each with a desired property. As shown in FIG. 20, for example, clad tubing 500 has a tantalum layer 502 over a stainless steel layer 504. The tantalum layer 502 provides radiodensity, thereby making a connector 10, 410, or 610 that is cut from tube 500 radiologically viewable. The stainless steel layer 504 provides rigidity to the connector. The medial section can be ground to reduce the thickness ratio to favor the tantalum. This improves the ability for balloon expansion. Although tube 500 (and the resulting connector 10, 410, or 610) may thus be made of two or more layers of different materials, the tube and the connector are still accurately described as unitary, one-piece, or integral. As an alternative to using clad tubing, the connector may be plated with a radiologic material to give it a desired radiodensity. Another example of a material suitable for radiologic layer 502 is platinum.

Figure 21:
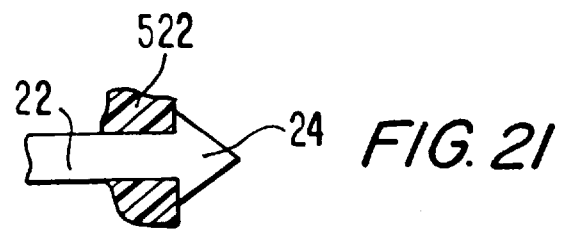
FIG. 21 is a simplified elevational view, partly in section, illustrating a possible modification of connectors in accordance with the invention.
Figure 22:
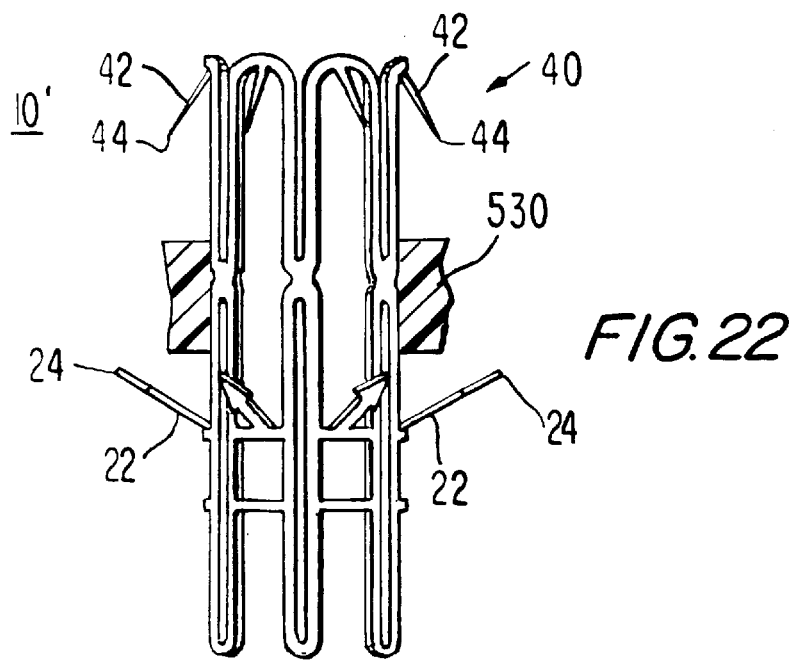
FIG. 22 is a simplified elevational view, partly in section, illustrating another possible modification of connectors in accordance with the invention.

Small polyester or other polymer patches or bands may be used on or in association with a connector of this invention to help seal and coagulate blood. Such patches may be inserted over individual fingers as shown, for example, at 522 in FIG. 21. Alternatively, such a band or web may be provided around the medial portion of connector 10, 410, or 610 as shown, for example, at 530 in FIG. 22. A band or web like 530 may also be used to constrain the size of the connector or a graft (such as a vein graft) relative to the connector. Vein grafts may dilate significantly under arterial blood pressure. A band or web can be used to fix its size relative to the connector. Alternatively or additionally a band or web like 530 can be provided to help seal the completed anastomosis. For purposes of these various kinds, a band or web like 530 may preferably be elastic (e.g., of a rubber or rubber-like material such as silicone or polyurethane). The band or web like 530 can be porous, if desired, and may be impregnated with drugs to facilitate healing and/or sealing. Similarly, polymer patches like 522 in FIG. 21 can include and release coagulant and/or other medication to help prevent bleeding and promote healing. Patches like 522 in FIG. 21 can help prevent members like 22 from pulling back through tissue that the member has penetrated.

An important attribute of the connectors of this invention is the characteristic that the medial section is soft enough to allow balloon expansion and strong enough to secure the two body fluid conduits via such elements as 22 and 42, 422 and 460/462/464, or 642. To achieve this with a single material and wall thickness, which may be preferable from a manufacturing perspective, the center section may be annealed selectively to soften it without compromising the rigidity of the retention elements (e.g., 22, 42, 422, 642, etc.). This can be done, for example, by laser heat treating the medial section only. The results of this process are relatively low hardness in the medial section and relatively high hardness in the end sections, all within an overall length of about 0.2 inches.

The connectors of this invention may also be made of a super-elastic material such as nickel-titanium ("nitinol"), which would allow a similar geometry as stainless steel to self-deploy or actuate in-vivo.

It will be appreciated that the fact that the connectors of this invention can be initially relatively small in circumference, and that they can be remotely controlled to position them in the patient and to then annularly expand them for final deployment, facilitates use of these connectors and associated apparatus (e.g., apparatus 200) at remote and/or inaccessible locations in a patient. For example, a connector of this invention may be delivered into and installed in a patient (using apparatus such as apparatus 200) through relatively small instrumentation such as laparascopic apparatus, a cannula, or an intraluminal catheter. Thus a connector and associated apparatus (e.g., apparatus 200) of this invention can be used in any of the procedures mentioned earlier in this specification, and in particular in procedures and with other elements shown in any of above-mentioned references WO 98/16161, U.S. Ser. Nos. 5,976, 178, 08/844,992, 08/869,808, and 09/187,364. Alternatively, the connector and/or apparatus (e.g., apparatus 200) of this invention can be used in more traditional or conventional surgical procedures or in other, known, less invasive or minimally invasive procedures. As just some examples of possible uses of the connectors and apparatus of this invention, they can be used to perform an anastomosis to a beating or still heart without the use of sutures or direct access.

Again, although the connectors of this invention can be made in various sizes for various uses, a typical connector is initially less than about 1 millimeter in diameter and in the range from about 2 to about 4 millimeters in length. After annular enlargement, a typical connector is more than about 2.5 millimeters in diameter. The pre-yield geometry of these connectors is ideal for delivery and positioning; the post-yield geometry is ideal for vessel securement, seal, and patency. The geometry of the connectors is ideal for annular enlargement. Radial outward deflection of certain connector members such as 22, 42, 422, 642, etc., is ideal for interfacing the expanding medial section of the connector to each of the two body fluid conduits to be connected (e.g., a graft vessel and an artery vessel).

As has been explained, certain connector cells may be configured to open before other cells as desired to optimize deployment positioning. Integral connector fingers such as 22, 42, 422, 642, etc., can be deflected radially out from the remainder of a connector for the purpose of attachment to body fluid conduits (e.g., a graft and an artery). These fingers are part of the connector body and can be hooks, barbs, loops, or spikes. The geometry of the fingers can also change, as desired, in response to balloon expansion. A balloon catheter can be used to actuate the connector and provide an anastomosis opening and attachment. The nose cone portion 220 of apparatus 200 covers the connector and graft interface, allowing dilation of the other body fluid conduit wall and passage of the connector through that wall. The connector provides the actual anastomotic opening and the connection simultaneously. The device is actuated via a balloon and catheter delivery system.

Among the advantages of the invention are that it eliminates suturing and reduces the time required to produce an anastomosis. In major circulatory system repair procedures such as cardiac bypass procedures, this can reduce cardiopulmonary pump time, which is of great benefit to the patient. The invention provides optimal flow dynamics, e.g., from a graft to the coronary artery. The blood entrance angle can be engineered into the connector geometry rather than relying on suture skill or technique. The invention eliminates possible suture injury to vessels. At the high stress site of an anastomosis sutures are eliminated. The connector and a graft can be delivered percutaneously, e.g., as in several of the references that are mentioned above. Direct access required for suturing is eliminated. An anastomotic connection can be made to a beating heart.

The invention claimed is:

1. A connector for use in making an anastomotic connection between tubular body fluid conduits in a patient comprising a unitary structure disposed annularly about a longitudinal axis and having axially spaced first and second portions, said first portion having a plurality of annularly spaced first members that are deflectable radially out from a remainder of said structure, said second portion having a plurality of annularly spaced second members that are deflectable radially out from a remainder of said structure, and said structure being configured for annular enlargement, in use, along its entire length parallel to the longitudinal axis.

2. The connector defined in claim 1 wherein said structure is configured for formation by removal of selected material from a single unitary tubular member.

3. The connector defined in claim 1 wherein said structure is further configured so that said annular enlargement reduces axial spacing between said first and second members.

4. The connector defined in claim 1 wherein the first members have free ends that point toward the second portion.

5. The connector defined in claim 4 wherein the second members have free ends that point toward the first portion.

6. The connector defined in claim 4 wherein the free ends of the first members are configured to penetrate a side wall of a first of the tubular body fluid conduits at locations that are annularly spaced around the anastomotic connection.

7. The connector defined in claim 6 wherein the second members have free ends that are configured to penetrate a side wall of a second of the tubular body fluid conduits at locations that are annularly spaced around the anastomotic connection.

8. The connector defined in claim 1 wherein the first members have free ends that are deflectable so that they point toward the second portion.

9. The connector defined in claim 8 wherein the second members have free ends that are deflectable so that they point toward the first portion.

10. The connector defined in claim 1 wherein said structure is configured for annular enlargement in response to inflation of a balloon disposed inside said structure.

11. The connector defined in claim 1 wherein said structure is configured for disposition substantially concentric with the anastomotic connection.

12. The connector defined in claim 11 wherein the first portion is configured for disposition substantially concentrically relative to an axial end portion of a first of the tubular body fluid conduits.

13. The connector defined in claim 12 wherein the second portion is configured for disposition through an aperture in a side wall of a second of the tubular body fluid conduits so that the anastomotic connection is an end-to-side connection between the first and second tubular body fluid conduits.

14. The connector defined in claim 11 wherein the first portion is configured for disposition through an aperture in a side wall of a first of the tubular body fluid conduits and the second portion is configured for disposition through an aperture in a side wall of a second of the tubular body fluid conduits so that the anastomotic connection is a side-to-side connection between the first and second tubular body fluid conduits.

15. The connector defined in claim 1 wherein the first members are plastically deflectable radially out from a remainder of said structure.

16. The connector defined in claim 15 wherein the second members are plastically deflectable radially out from a remainder of said structure.

17. The connector defined in claim 1 wherein said structure is configured for plastic annular enlargement.

18. The connector defined in claim 1 wherein said structure has axially spaced first and second segments configured to annularly enlarge in response to respective different first and second amounts of applied annular enlargement force.

19. The connector defined in claim 1 wherein said first members are configured for deflection radially out from a remainder of said structure in response to inflation of a balloon disposed inside said structure.

20. The connector defined in claim 1 wherein said first members have free end portions that are configured to facilitate penetration of a side wall of at least one of said tubular body fluid conduits.

21. The connector defined in claim 20 wherein the free end portions of said first members are sharply pointed to facilitate penetration of the side wall of said at least one tubular body fluid conduit.

22. The connector defined in claim 20 wherein said free end portions of the first members are configured to resist withdrawal from the side wall of said at least one tubular body fluid conduit after penetration of said side wall.

23. The connector defined in claim 1 wherein each of said first members comprises a U-shaped component, the legs of the U remote from the base of the U being connected to respective parts of a remainder of the structure that are configured to annularly separate from one another when the structure is annularly enlarged.

24. The connector defined in claim 1 wherein said structure comprises a plurality of annularly spaced axially extending component members, each of which is connected to a first associated annularly adjacent component member at first and second axially spaced locations, and each of which is connected to a second associated annularly adjacent component member at a third location which is axially medial said first and second locations.

25. The connector defined in claim 24 wherein said structure is configured for annular enlargement by deforming each of said component members to increase the annular space between that component member and the first associated component member adjacent the third location and to increase the annular space between that component member and the second associated component member adjacent the first and second locations.

26. The connector defined in claim 24 wherein each of the first members is joined to a remainder of said structure adjacent a respective one of the first locations.

27. The connector defined in claim 26 wherein each of the second members is joined to a remainder of said structure adjacent a respective one of the second locations.

28. The connector defined in claim 1 wherein the unitary structure comprises first and second layers, each of which is substantially concentric with said longitudinal axis, said first and second layers being adjacent to one another radially from said longitudinal axis.

29. The connector defined in claim 28 wherein said first layer is made of a material selected for its radiologic properties, and wherein said second layer is made of a material selected for its mechanical properties.

30. The connector defined in claim 2 wherein said tubular member is clad tubing.

31. The connector defined in claim 30 wherein said clad tubing has a first annular layer selected for its radiologic properties and a second layer concentric with the first layer and selected for its mechanical properties.

32. The connector defined in claim 1 further comprising a body of medicine-releasing material disposed on the unitary structure.

33. The connector defined in claim 32 wherein the medicine-releasing material comprises a polymer.

34. The connector defined in claim 33 wherein the body of medicine-releasing material comprises a band disposed annularly around the unitary structure.

35. The connector defined in claim 32 wherein the first members are configured to penetrate a side wall of a first of the tubular body fluid conduits, and wherein the body of medicine-releasing material includes portions disposed on the first members where the first members are configured to penetrate the side wall of the first tubular body fluid conduit.

36. The connector defined in claim 1 further comprising a band of elastic material disposed annularly around the unitary structure.

37. A connector for use in making an anastomotic connection between tubular body fluid conduits in a patient comprising a unitary structure disposed annularly about a longitudinal axis and having axially spaced first and second portions, said first portion having a plurality of annularly spaced first members that are deflectable radially out from a remainder of said structure, and said structure being configured to be annularly enlarged and to respond to such annular enlargement by decreasing in axial spacing between said first and second portions.

38. The connector defined in claim 37 wherein said structure is configured for formation by removal of selected material from a single unitary tubular member.

39. The connector defined in claim 37 wherein the first members have free ends that point toward the second portion.

40. The connector defined in claim 37 wherein the first members have free ends that are configured to penetrate a side wall of a first of the tubular body fluid conduits.

41. The connector defined in claim 37 wherein the first members have free ends that are configured to penetrate a side wall of a first of the tubular body fluid conduits at locations that are annularly spaced around the anastomotic connection.

42. The connector defined in claim 37 wherein the first members have free ends that are deflectable so that they point toward the second portion.

43. The connector defined in claim 37 wherein said structure is configured to be annularly enlarged by inflation of a balloon disposed inside said structure.

44. The connector defined in claim 37 wherein said structure is configured for disposition substantially concentric with the anastomotic connection.

45. The connector defined in claim 37 wherein the first portion is configured for disposition through an aperture in a side wall of a first of the tubular body fluid conduits.

46. The connector defined in claim 45 wherein the second portion is configured for disposition substantially concentrically relative to an axial end portion of a second of the tubular body fluid conduits so that the anastomotic connection can be an end-to-side connection between the first and second tubular body fluid conduits.

47. The connector defined in claim 45 wherein the second portion is configured for disposition through an aperture in a side wall of a second of the tubular body fluid conduits so that the anastomotic connection can be a side-to-side connection between the first and second tubular body fluid conduits.

48. The connector defined in claim 37 wherein the first members are plastically deflectable radially out from a remainder of said structure.

49. The connector defined in claim 37 wherein said structure is configured for plastic annular enlargement.

50. The connector defined in claim 37 wherein said structure has axially spaced first and second segments configured to annularly enlarge in response to respective different first and second amounts of applied annular enlargement force.

51. The connector defined in claim 37 wherein said first members are configured for deflection radially out from a remainder of said structure in response to inflation of a balloon disposed inside said structure.

52. The connector defined in claim 37 wherein said first members have free end portions that are configured to facilitate penetration of a side wall of at least one of said tubular body fluid conduits.

53. The connector defined in claim 52 wherein the free end portions of said first members are sharply pointed to facilitate penetration of the side wall of said at least one tubular body fluid conduit.

54. The connector defined in claim 52 wherein the free end portions of the first members are configured to resist withdrawal from the side wall of said at least one tubular body fluid conduit after penetration of said side wall.

55. The connector defined in claim 37 wherein each of said first members comprises a U-shaped component, the legs of the U remote from the base of the U being connected to respective parts of a remainder of the structure that are configured to annularly separate from one another when the structure is annularly enlarged.

56. The connector defined in claim 37 wherein said structure comprises a plurality of annularly spaced, axially extending component members, each of which is connected to a first associated annularly adjacent component member at first and second axially spaced locations, and each of which is connected to a second associated annularly adjacent component member at a third location which is axially medial said first and second locations.

57. The connector defined in claim 56 wherein said structure is configured to be annularly enlarged by deforming each of said component members to increase the annular space between that component member and the first associated component member adjacent the third location and to increase the annular space between that component member and the second associated component member adjacent the first and second locations.

58. The connector defined in claim 56 wherein each of the first members is joined to a remainder of said structure adjacent a respective one of the first locations.

59. The connector defined in claim 37 wherein the unitary structure comprises first and second layers, each of which is substantially concentric with said longitudinal axis, said first and second layers being adjacent to one another radially from said longitudinal axis.

60. The connector defined in claim 59 wherein said first layer is made of a material selected for its radiologic properties, and wherein said second layer is made of a material selected for its mechanical properties.

61. The connector defined in claim 38 wherein said tubular member is clad tubing.

62. The connector defined in claim 61 wherein said clad tubing has a first annular layer selected for its radiologic properties and a second layer concentric with the first layer and selected for its mechanical properties.

63. The connector defined in claim 37 further comprising a body of medication-releasing material disposed on the unitary structure.

64. The connector defined in claim 63 wherein the medication-releasing material comprises a polymer.

65. The connector defined in claim 64 wherein the body of medication-releasing material comprises a band disposed annularly around the unitary structure.

66. The connector defined in claim 63 wherein the first members are configured to penetrate a side wall of a first of the tubular body fluid conduits, and wherein the body of medication-releasing material includes potions disposed on the first members where the first members are configured to penetrate the side wall of the first tubular body fluid conduit.

67. The connector defined in claim 37 further comprising a band of elastic material disposed annularly around the unitary structure.

* * * * *